United States Patent
Aberg et al.

(10) Patent No.: US 9,694,003 B2
(45) Date of Patent: Jul. 4, 2017

(54) FORMULATIONS AND METHODS FOR TREATING HIGH INTRAOCULAR PRESSURE

(71) Applicant: Bridge Pharma, Inc., Sarasota, FL (US)

(72) Inventors: A.K. Gunnar Aberg, Sarasota, FL (US); Vincent B. Ciofalo, Branford, CT (US); Keith Johnson, Durham, NC (US)

(73) Assignee: BRIDGE PHARMA, INC., Sarasota, FL (US)

( * ) Notice: Subject to any disclaimer, the term of this patent is extended or adjusted under 35 U.S.C. 154(b) by 0 days.

(21) Appl. No.: 15/071,819

(22) Filed: Mar. 16, 2016

(65) Prior Publication Data

US 2017/0105987 A1    Apr. 20, 2017

Related U.S. Application Data

(60) Provisional application No. 62/241,938, filed on Oct. 15, 2015.

(51) Int. Cl.
*A61K 31/445* (2006.01)
*A61K 31/4535* (2006.01)
*A61K 9/00* (2006.01)
*A61K 45/06* (2006.01)
*A61K 9/06* (2006.01)
*A61K 9/107* (2006.01)

(52) U.S. Cl.
CPC ........ *A61K 31/4535* (2013.01); *A61K 9/0043* (2013.01); *A61K 9/0048* (2013.01); *A61K 9/06* (2013.01); *A61K 9/107* (2013.01); *A61K 45/06* (2013.01)

(58) Field of Classification Search
CPC .................................................. A61K 31/4535
See application file for complete search history.

(56) References Cited

U.S. PATENT DOCUMENTS

| | | |
|---|---|---|
| 7,226,934 B1 | 6/2007 | Aberg et al. |
| 7,557,128 B2 | 7/2009 | Aberg et al. |
| 8,741,930 B2 | 6/2014 | Aberg et al. |
| 8,765,787 B2 | 7/2014 | Aberg et al. |
| 8,969,385 B2 | 3/2015 | Aberg et al. |

OTHER PUBLICATIONS

Baudouin et al.; "Preservatives in Eyedrops: The Good, the Bad, and the Ugly"; Progress in Retinal and Eye Research; 29; pp. 312-324; (2010).
Baudouin; "Detrimental Effect of Preservatives in Eyedrops: Implications for the Treatment of Glaucoma"; Acta Ophthalmol.; 86; pp. 716-726; (2008).
Choy et al.; "Cytotoxicity of Rigid Gas-permeable Lens Care Solutions"; Clinical and Experimental Optometry; 96; pp. 467-471; (2013).
Gelatt et al.; "Prevalence of the Breed-related Glaucomas in Purebred Dogs in North America"; Vet Ophthalmol; 7 (2); pp. 97-111; (2004), Abstract only.
Hamard et al.; "In Vitro Effects of Preserved and Unpreserved Antiglaucoma Drugs on Apoptotic Marker Expression by Human Trabecular Cells"; Graefe's Arch Clin Exp Ophthalmol; 241; pp. 1037-1043; (2003).
Hoyng et al.; "The Additive Intraocular Pressure-lowering Effect of Latanoprost in Combined Therapy with Other Ocular Hypotensive Agents"; Surv Ophthalmol.; 41 Suppl 2; S93-8; (1997) Abstract only.
Michee et al.; "Effects of Benzalkonium Chloride on THP-1 Differentiated Macrophages In Vitro"; PLOS ONE 8(8); e72459; (2013).
Myers et al.; "Update on Sustained-Release Drug Therapies"; Glaucoma Today; Jan./Feb. 2016; pp. 41-44; (2016).
Okeke et al.; "Adherence With Topical Glaucoma Medication Monitored Electronically"; Ophthalmology; 116(2); pp. 191-199; (2009).
Quigley et al.; "The Number of People with Glaucoma Worldwide in 2010 and 2020"; Br J Ophthalmol.; 90(3); pp. 262-267; (2006).
Robin et al.; "Compliance and Adherence in Glaucoma Management"; Indian Journal of Ophthalmology: 59(Suppl 1); pp. S93-S96; (2011).
Sarkar et al.; "Corneal Neurotoxicity Due to Topical Benzalkonium Chloride"; Invest Ophthalmol Vis Sci. 53(4); pp. 1792-1802; (2012); Abstract only.
Tanihara et al.; "One-year Clinical Evaluation of 0.4% Ripasudil (K-115) in Patients with Open-angle Glaucoma and Ocular Hypertension"; Acta Ophthalmol. 94(1); e26-34; (2016).
The Merck Manual of Diagnosis and Therapy, 18th Ed., Richard K. Albert, ed., 103 Glaucoma, pp. 903-910, (2006).
Tokushige et al.; "Effectsof Topical Administration of Y-39983, a Selective Rho-Associated Protein Kinase Inhibitor, on Ocular Tissues in Rabbits and Monkeys"; Invest Ophthal Vis Sci; 48; pp. 3216-3222; (2007).
Waldvogel et al.; Untersuchungen uber synthetische Arzneimittel 9- and 10-Oxo-Derivate von 9,10-Dihydro-4H-benzo[4,5]cyclohepta-[1,2-b]thiophenen, Helvetica Chimica Acta, 59; pp. 866-877; (1976) with English abstract.

(Continued)

*Primary Examiner* — Zohreh Fay
(74) *Attorney, Agent, or Firm* — Cantor Colburn LLP

(57) ABSTRACT

Disclosed herein are methods of treating a mammal in need of a reduction in intraocular pressure by administering an intraocular formulation including a therapeutically effective amount of norketotifen for the reduction of intraocular pressure to the eye of the mammal in need thereof, wherein the intraocular formulation includes about 0.02 wt % to about 1.0 wt % norketotifen or a salt or an isomer thereof, calculated as the norketotifen free base. In certain aspects, the intraocular formulation is free from any added preservative and the intraocular formulation is self-preserving. Also included herein is a method of treating a human in need of a reduction in intraocular pressure by administering an intranasal formulation that includes a therapeutically effective amount of norketotifen for the reduction of intraocular pressure to the eye of the human in need thereof. Also, the beneficial effects of known drugs for high IOP are improved by co-administration with norketotifen.

13 Claims, No Drawings

(56) References Cited

OTHER PUBLICATIONS

Williams, RD et al.; "Ocular Hypotensive Effect of the Rho Kinase Inhibitor AR-12286 in Patients with Glaucoma and Ocular Hypertension"; Am J Ophthalmol.; 152(5); 834-841; (2011); Abstract only.

Zawinka et al.; "Intravenously Administered Histamine Increases Choroidal but not Retinal Blood Flow"; Investigative Ophthalmology & Visual Science; 45(7); pp. 2337-2341; (2004).

International Search Report and Written Opinion; International Application No. PCT/US2016/055404; International filing Date Oct. 5, 2016; Date of Mailing Dec. 16, 2016; 10 pages.

FORMULATIONS AND METHODS FOR TREATING HIGH INTRAOCULAR PRESSURE

CROSS-REFERENCE TO RELATED APPLICATIONS

This application claims priority to U.S. Provisional Application 62/241,938 filed on Oct. 15, 2015, which is incorporated herein by reference in its entirety.

TECHNICAL FIELD

Disclosed herein are methods of treating patients suffering from high intraocular pressure (IOP), with or without concomitant glaucoma.

BACKGROUND

The disorders that are called glaucoma cause a progressive loss of retinal ganglion cells (RGC) and their axons, which initially leads to loss of peripheral vision, and ultimately leads to complete blindness. It is estimated that glaucoma will affect about 80 million people worldwide in year 2020. Worldwide, glaucoma is the second-leading cause of blindness after cataracts, and it is the leading cause of blindness among African Americans. Glaucoma has a significantly higher prevalence in people of more than 60 years of age than in younger people.

Glaucoma disorders can be divided into two categories: "open-angle glaucoma" and "closed-angle glaucoma". Open-angle glaucoma is painless and develops slowly over time and has no symptoms until the disease has progressed significantly. Closed-angle glaucoma causes sudden pain, redness, nausea and vomiting with the intraocular pressure suddenly increasing, causing a medical emergency. Closed-angle glaucoma accounts for less than 10 percent of glaucoma cases in the United States and as many as half of all glaucoma cases in some Asian countries. The Merck Manual, $18^{th}$ Edition, 2006, pages 903-910, describes different types glaucoma and the signs and symptoms of glaucoma.

The underlying cause of glaucoma is unknown. However, the single major risk factor, and the major focus of treatment, is elevated intraocular pressure (IOP). Intraocular pressure, also called ocular pressure, is a function of two factors: the production of the aqueous humor from the ciliary processes of the eye and the drainage of the same fluid out of the eye through the trabecular meshwork. The diagnosis of glaucoma includes measurements of intraocular pressure (tonometry), anterior chamber angle examination (gonioscopy), and examination of the optic nerve for visible damage. Elevated IOP is believed to lead to damage of the optic nerve and is therefore considered to be a causative factor for the development of glaucoma.

IOP is often increased because the drainage of the fluid in the eye through the trabecular mesh is impaired. Preservative compounds, and particularly benzalkonium chloride (BAK) that are presently used in ocular formulations have been shown to damage the trabecular mesh at concentration that are 100 times lower than the concentrations presently used in dropper-bottles by glaucoma patients. Thus, for diseases related to increased IOP such as glaucoma, it is critical to develop preservative-free therapeutic formulations.

What is needed are compositions and methods for reducing elevated intraocular pressure, with and without concomitant glaucoma, in therapeutically effective formulations that are free from preservatives.

SUMMARY

In one aspect, a method of treating a mammal in need of a reduction in intraocular pressure comprises administering an intraocular formulation comprising a therapeutically effective amount of norketotifen for the reduction of intraocular pressure to the eye of the mammal in need thereof, wherein the intraocular formulation comprises about 0.02 wt % to about 1.0 wt % norketotifen or a salt or an isomer thereof, wherein the amount of norketotifen is calculated as the norketotifen free base, wherein the intraocular formulation is free from any added preservative, wherein the intraocular formulation is self-preserving.

In another aspect, a method of treating a human in need of a reduction in intraocular pressure comprises administering an intranasal formulation comprising a therapeutically effective amount of norketotifen for the reduction of intraocular pressure to the eye of the human in need thereof, wherein the intranasal formulation comprises about 0.02 wt % to about 1.0 wt % norketotifen, a salt or isomer thereof, wherein the amount of norketotifen is calculated as the norketotifen free base.

DETAILED DESCRIPTION

Disclosed herein are methods of administering norketotifen for the reduction of IOP, such as the treatment of patients with conditions of high IOP, using ophthalmic compositions, specifically intraocular compositions, containing norketotifen. Ophthalmic formulations that are designed to deliver norketotifen to intraocular biophases are herein referred to as "intraocular formulations", although such formulations are delivered as regular eye drops into the conjunctival sac of the eye, from where said intraocular formulations, containing the therapeutically active ingredient, are penetrating into the eye. It was surprisingly found in a four-week toxicological study that an intraocular eye drop formulation containing norketotifen decreased intraocular pressure with high statistical significance. A complete lack of concomitant ocular irritation and ophthalmic toxicity was found in the same study. It has also been found that the beneficial effects of known drugs for high IOP are improved by co-administration with norketotifen.

Glaucoma is a term for a group of eye disorders, which result in damage to the optic nerve. The management of glaucoma has the goals of avoiding optical nerve damage, preserving visual field and improving the quality of life for the patients while minimizing the risk for drug-induced adverse events. The damage to the optic nerve is most often due to increased pressure in the eye. Presently, lowering IOP is the mainstay of glaucoma treatment. The treatment of glaucoma patients generally consists of lowering the IOP and the therapeutic target is usually a lowering of the IOP by about 20 to 30 percent, preferably about 30 percent.

Glaucoma is defined as a disease with progressive damage to the optic nerve, which may be caused by high IOP and which ultimately results in total loss of vision. Humans, dogs and cats have normal IOP between about 10 and 21 mmHg. The terms "increased IOP" and "elevated IOP" and "high IOP" refer to IOP that is higher than the normal IOP for the species or for an individual. Human glaucoma patients most often have intraocular pressures of 21-28 and IOP in glaucomatose dogs and cats is often 30 mmHg and higher. IOP in dogs can reach 50 mmHg and higher and permanent loss of vision can occur within hours in dogs if the IOP is very high.

Also glaucoma patients with normal IOP benefit from reduction of IOP as demonstrated in an international multicenter study of glaucoma patients that was completed in 1998. This study demonstrated that lowering of IOP by 30 percent slowed or halted the progression of optic nerve damage in glaucoma patients, even in glaucoma patients with normal IOP.

Norketotifen is a metabolite of ketotifen (Zaditor®, Novartis), which is used as an ophthalmic medication to decrease ocular pruritus in patients suffering from allergic conjunctivitis. Ketotifen has potent histamine H-1 receptor inhibitory activity, while norketotifen inhibits both histamine H-1 and H-4 receptors. Norketotifen is one of the metabolites that are formed in the liver after oral administration of ketotifen.

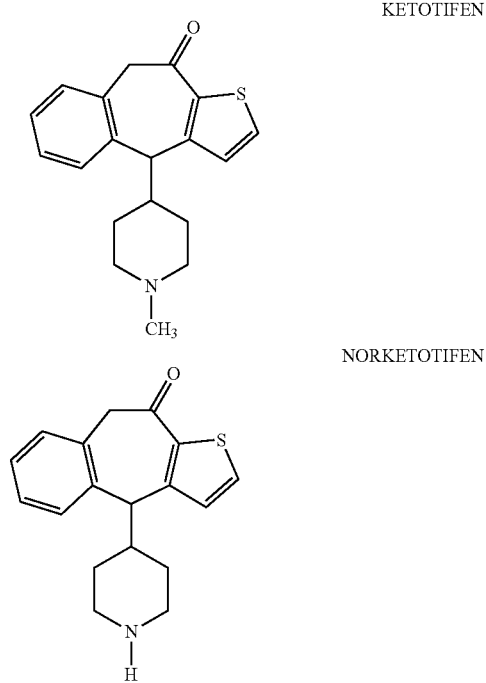

Ketotifen is available commercially, for example from Sigma-Aldrich. Norketotifen can be made by demethylation of ketotifen according to methods known in the art. S-norketotifen and R-norketotifen are described in U.S. Pat. Nos. 7,226,934 and 7,557,128, respectively. RS-norketotifen is hereinafter also called norketotifen. Chemically, norketotifen is 4-(4-piperidyliden)-9-oxo-9,10-dihydro-4H-benzo[4,5]cyclohepta[1,2-b]thiophene, which is a racemic mixture of the active isomers R-norketotifen and S-norketotifen.

As described in U.S. Pat. No. 8,969,385, racemic norketotifen is useful for the treatment of allergic conjunctivitis. U.S. Pat. Nos. 8,741,930 and 8,765,787 are incorporated herein by reference for their disclosure of the ophthalmic use of norketotifen for the treatment of dry eye syndromes (xerophthalmia). Due to its physicochemical properties and its pharmacological effects, such as low anti-muscarinic activity, norketotifen is well suited for ophthalmic use.

Therapeutically effective ophthalmic compositions (formulations) for the treatment of patients with high IOP and glaucoma should deliver norketotifen or a salt thereof to intraocular biophases. Ophthalmic formulations that are designed to deliver norketotifen to the intraocular biophases are herein referred to as "intraocular formulations". Thus, intraocular compositions are a subset of ophthalmic compositions that contain concentrations of active agent (norketotifen) and excipients that facilitate delivery of the active agent to the intraocular biophases, that is, the formulations allow the active agent to penetrate through the cornea and/or the sclera into the eye and not simply contact the outside of the eye. In particular, an intraocular formulation should allow the active agent to contact the biophases where the ocular fluid is secreted (the ciliary process) and where the ocular fluid is excreted out of the eye (the trabecular mesh). Intraocular compositions can be applied to the mucous membranes surrounding the eye, or can be applied to the cornea as long as the compositions are capable of delivering norketotifen to the intraocular biophases. Intraocular compositions include aqueous and non-aqueous solutions, ocular gels, and ocular emulsions as described herein. In a specific embodiment, the intraocular compositions containing norketotifen are self-preserving and can be used without added preservatives.

Although hundreds of ophthalmic excipients exist, it is far from obvious what excipients may be compatible with norketotifen and what combinations of excipients and what concentrations thereof should be used to obtain intraocular delivery of norketotifen or an active salt or isomer thereof while simultaneously minimizing the ocular side effects of the drug and the excipients of the norketotifen formulations. Intraocular delivery presents different challenges than ophthalmic delivery intended for biophases in front of the eye, such as medications for conjunctivitis or xerophthalmia. Each composition has to be designed to deliver the medication to its biophase, keeping in mind the anatomical penetration barriers and the physicochemical and the pharmacological properties of the active molecule(s). Exemplary formulations are provided in Tables 2-5.

The intraocular compositions described herein include norketotifen formulated together with carefully selected excipients. The intraocular formulations of norketotifen disclosed herein are intended to reach intraocular biophases in the eyes of patients suffering from elevated IOP. The intraocular norketotifen formulations can be manufactured by standard manufacturing processes that are well known to those skilled in the art of manufacturing ophthalmic dosage forms.

The intraocular formulations contain a carrier, such as water which is the carrier for an aqueous solution. Non-aqueous carriers include polyethylene glycol (PEG) and/or propylene glycol (PG) can be used in ophthalmic compositions. Norketotifen HF was found to be soluble in a polyethylene glycol (PEG 300) up to about 0.15 percent w/w. Propylene glycol can be used as a solvent to obtain high concentrations of norketotifen in ophthalmic ointments and gels since norketotifen HF, has been found to be soluble in propylene glycol up to 1.0 wt %. Norketotifen can be dissolved in water in concentrations up to about 0.2 wt %. Exemplary non-aqueous solvents include polyethylene glycol (about 0.1% to about 90%) and propylene glycol (about 0.1% to about 90%).

The norketotifen intraocular formulations may comprise one or more of a chelating agent, a stabilizing agent, a buffering agent, a tonicity adjusting agent, a solubilizing agent, a viscosity-adjusting agent, a humectant, an antioxidant, an emollient, a gelling agent, and in situ gelling agent, a lubricant, a mucoadhesive, or combinations thereof. For solution formulations, the amounts included below are wt %.

Chelating agents or sequestering agents have the ability to form a chelate complex with a substrate. Known chelating agents are for example, edetate, proteins, polysaccharides, polynucleic acids and chelating polymers. Exemplary chelating agents compatible with norketotifen are edetate and chitosan polysaccharides. If desired, chelating agents may be used in amounts of about 0.01 wt % to about 10 wt %, specifically about 0.01 wt % to 2.0 wt %. Some chelating agents, for example chitosan polysaccharides, also have mucoadhesive properties. The term "EDTA", as used herein, comprises the chemical compound ethylenediaminetetraacetic acid and the disodium and calcium disodium salts thereof. EDTA and the salts thereof have many names, such as for example edetate, disodium edetate. ED3A (ethylenediaminetriacetic acid) may be used instead of or in addition to EDTA in the compositions described herein.

Stabilizing agents enhance the physical stability of ocular formulation, such as for example emulsions, but are not known to influence the long-term stability of any specific component of the formulations. Some known stabilizers, such as for example xanthan gum and carbomers (acrylic acid polymers), were not optimal for use with norketotifen since hazy suspensions were formed. Exemplary stabilizers that are compatible with norketotifen include methylcellulose, edetate, chitosan, hydroxypropylmethylcellulose and hydroxyethylcellulose. Edetate functions both as a chelator and a stabilizing agent, for example. Terms, such as "stabilization", "stabilizer", "stability", when used herein relate to the stability of the pharmaceutical formulation in total when exposed to storage, oxygen, air, light and or heat (including high-temperature sterilization, such as autoclaving). Stabilizers listed here are useful in concentrations of about 0.05 wt % to about 4 wt %, and are specifically used in concentrations of about 0.05 wt % to about 2 wt %.

Solubilizers improve the solubility of norketotifen in the ophthalmic formulations. In some embodiments, combined stabilizer/solubilizers may be used in formulations containing norketotifen. Combined stabilizer/solubilizers are for example cyclodextrins. Exemplary cyclodextrins include α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin. The amounts are generally about 0.01 wt % to about 90 wt %, more specifically of about 0.1 wt to about 20 wt %.

Buffering agents are used to adjust the pH of a composition. The function of a buffering agent is to drive an acidic or alkaline solution to a certain pH range and prevent a change from this pH. Buffering agents have variable properties—some are more soluble than others; some are acidic while others are basic. Exemplary buffering agents that are compatible with norketotifen include phosphates, boric acid, borates, citrates and acetates. Buffers are generally used in the concentrations needed to stabilize the acidity to about pH 4.0 to about pH 6.0, specifically about pH 5.0 to about pH 6.0. The concentration of each of the buffering compounds is about 0.01 wt % to about 4 wt %, specifically about 0.05 wt % to about 1 wt %. The acidity of all formulations described herein can be adjusted by changing the concentrations of the buffering agents or by adding an acid or a base as known to those skilled in the art.

Tonicity-adjusting agents increase the effective osmolarity or effective osmolality of a formulation. Hypertonic, hypotonic and isotonic solutions are defined in reference to a cell membrane by comparing the tonicity of the solution with the tonicity within the cell. Ocular compositions may contain a tonicity-adjusting agent in an amount sufficient to cause the final composition to have an ophthalmically acceptable osmolality (generally about 150 to about 450 mOsm and preferably about 230 to about 330 mOsm). Exemplary tonicity-adjusting agents to be used with norketotifen may be of ionic and/or non-ionic type. An example of ionic type tonicity enhancers is sodium chloride and examples of non-ionic tonicity enhancing agents are, for example sorbitol and propylene glycol, which are compatible with norketotifen. Thus, norketotifen formulations may include, for example sodium chloride, in amounts of about 0.1 wt % to about 0.9 wt %, sorbitol in amounts of about 0.1% to about 10%, or propylene glycol in amounts about 0.1 wt % to about 10 wt %. If desired, compatible tonicity-adjusting agents can be used in all formulations mentioned herein. All ophthalmic formulations of norketotifen were adjusted to be approximately iso-osmotic to human tears.

Viscosity-adjusting agents increase the internal friction ("thickness") of a formulation, that is, they increase the viscosity of the formulations. The term "hydrogels" is often used for viscosity enhancing excipients, particularly in artificial tears and refers to a colloid with high gelling ability. Ophthalmic solutions may contain one or more viscosity-adjusting agents and have a viscosity of about 1.0 to about 100,000 cP, specifically about 2.0 to about 90,000 cP, and more specifically about 2.5 and about 75,000 cP, which is acceptable since compositions in this range of viscosity feel comfortable to the eye and do not cause blurring of the vision. Viscosified solutions are accepted to a great degree by patients, mainly because of the ease of administration. Some viscosity-adjusting agents, such as for example xanthan gum, are not as compatible with norketotifen as others. Viscosity modifying agents that are compatible with norketotifen include edetate, methylcellulose, carboxymethylcellulose, hydroxypropyl methylcellulose, hydroxyethyl cellulose, polyethylene glycol, propylene glycol alginate, chitosan, and tragacanth. As known to those skilled in the art, certain viscosity-adjusting agents such as for example edetate are multifunctional additives. If needed, compatible viscosity-adjusting agents can be used in all formulations mentioned herein. When desired, the amounts of the selected viscosity modifying agents are about 0.1 wt % to about 10 wt %, specifically 1 wt % and 5 wt %. Sorbitol, for example, may be used as a combined tonicity-adjusting and viscosity-adjusting excipient in an amount of about 0.1 wt % to about 10 wt %, specifically about 2 wt % to about 5 wt %.

Humectants can be used to soften biological tissues as they increase the water-holding capacity of ocular tissues, such as the cornea and the conjunctival membranes and certain humectants were found to be compatible with norketotifen and can be used in ocular formulations of norketotifen. Exemplary humectants that are compatible with norketotifen include polyethylene glycol, sorbitol and propylene glycol. When desired, compatible humectants can be used in all formulations mentioned herein. Humectants are used in amounts of about 0.05 wt % to about 10 wt %, specifically about 0.1 wt % to about 4 wt %, and more specifically about 0.1 wt % to about 2 wt %.

Antioxidants are compounds that act to slow or prevent the oxidation of other chemicals. Exemplary antioxidants that are compatible with norketotifen include sulfites, ascorbates, acetylcysteine, butylated hydroxyanisole (BHA) and butylated hydroxytoluene (BHT). When desired, compatible antioxidants can be used in all formulations mentioned herein. Useful concentrations of antioxidants are about 0.05 wt % to about 3 w %, specifically about 0.1 wt % to about 0.25 wt %.

Emollients cause occlusion of mucous membranes by providing a layer of oil to slow water loss from mucous membranes of the eye. Emollients also act as humectants and thereby improve the water-holding capacity of the ocular tissues. Emollients also act as lubricants, whereby these agents add slip or glide to the mucous membranes of the cornea and the conjunctival membranes. Exemplary emollients compatible with norketotifen include glycerin, propylene glycol, and hypromellose (hydroxypropyl methylcellulose, HPMC). When desired, compatible emollients can be used in all formulations mentioned herein. Emollients can be used in amounts of about 0.1 wt % to about 10 wt %, specifically in amounts of about 0.1 wt % to about 2 wt %.

Gelling agents (viscosity-modifying agents) are used to thicken and stabilize liquid solutions, emulsions and suspensions, thereby inducing retention of the compositions in the ocular tear film. Gelling agents dissolve in solutions, giving an appearance of a more or less solid matter, while being mostly composed of a liquid. Exemplary gelling agents that are compatible with norketotifen include edetate (EDTA), alginic acid and alginates, carrageenan, pectin, gelatin and gelling polymers. When desired, compatible gelling agents can be used in all formulations mentioned herein. Gelling agents can be used in concentrations from about 0.05 wt % to about 10 wt %, specifically in amounts of about 0.1 wt % to about 2.5 wt %.

In situ gelling agents may be included in ocular formulations of norketotifen and are instilled as drops into the eye and undergo sol-to-gel transition in the tear fluid, due, for example, to ion-triggered activation, pH-triggered activation or thermal activation. For example, alginate is a gelling agent that can be used in combination with the viscosity-enhancing agent hydroxypropyl methylcellulose (HPMC). The rheological behavior of the alginate/HPMC solutions were retained in the presence of norketotifen and was found to be a useful ion-activated in situ gelling system for norketotifen-containing compositions. Polyacrylic acid (Carbopol) is a gelling agent in combination with the viscosity-enhancing agent hydroxypropyl methylcellulose (HPMC) and is a useful pH-triggered in situ gelling system for norketotifen-containing compositions. Poloxamer 407 is a polymer with a solution viscosity that increases when its temperature is raised to the eye temperature. The temperature-sensitive rheological behavior of Poloxamer 407 or Poloxamer 407/188 mixtures was not influenced by the presence of norketotifen. Exemplary in situ gelling agents compatible with norketotifen were also found to include alginate/hydroxypropyl methylcellulose, polyacrylic acid/hydroxypropyl methylcellulose. In situ gelling agents can be used in amounts of about 0.5 wt % to about 10 wt %, specifically about 0.1 wt % to about 2.5 wt %. Poloxamers can be used in higher concentrations, up to about 25 wt %.

Lubricants can hold moisture on the eye. Numerous polymers can be used as ocular lubricants. Exemplary lubricants that are compatible with norketotifen include methylcellulose, hydroxypropylmethylcellulose, hydroxyethylcellulose, thiolated acrylic acid polymers, carbomer, carboxymethylcellulose sodium, chitosans, and polyisobutylcyanoacrylate. When desired, compatible lubricants can be used in all formulations mentioned herein. When used, the amount of lubricant is about 0.1 wt % to about 10%, specifically about 0.1 wt % to about 4 wt %, and more specifically about 0.1 wt % to about 2 wt %.

Mucoadhesive agents refer to materials that will adhere to mucus and mucosal membranes. Exemplary mucoadhesives that are compatible with norketotifen formulations include thiolated acrylic acid polymers, chitosan, polyisobutylcyanoacrylate and ethylcellulose. Mucoadhesive polymers, such as mucoadhesive chitosan and mucoadhesive chitosan-coated microspheres or liposomes are useful for prolonged delivery of norketotifen to the eye. Mucoadhesive agents are used in amounts of about 0.1 wt % to about 10 wt %, specifically about 0.1 wt % to about 2 wt %. If desired, compatible mucoadhesive agents can be used in all formulations mentioned herein. Using compatible mucoadhesive agents, norketotifen can be administered to patients as ocular mucoadhesive minitablets, microspheres and as ocular gel-forming minitablets.

Surfactants reduce the surface tension of liquids, such as for example water. Exemplary surfactants that are compatible with norketotifen include nonionic surfactants, such as for example polysorbates, glyceryl stearate, lecithins, polyethoxylated castor oil derivatives and oxyethylated tertiary octylphenol formaldehyde polymers, which in combinations with norketotifen were all found to be less irritating to the eye than ionic surfactants, which may also be used. If desired, compatible surfactants can be used in all formulations mentioned herein. Surfactants may be used in amounts of about 0.05 wt % to about 4 wt %, specifically about 0.1 wt % to about 2 wt %.

The ophthalmic formulations include norketotifen as a free base or as a pharmaceutically acceptable salt. Pharmaceutically acceptable salts of norketotifen include a hydrogen fumarate (HF), a hydrochloride, a hydrobromide, a hydrogen maleate, or a hydrogen sulfate. More preferred salts of norketotifen are the hydrochloride salts and the hydrogen fumarate salt. Most preferred is the hydrogen fumarate salt. The term "pharmaceutically acceptable salt" and the like refer to salts prepared from pharmaceutically acceptable acids, such as for example fumaric, hydrobromic, hydrochloric, maleic and sulphuric acids. As used herein, all percentages of norketotifen are based on norketotifen free base.

Norketotifen for intraocular administration can be in the form of an aqueous or nonaqueous solution, hydrophilic and hydrophobic gels/ointments, and emulsions, for example. Norketotifen can also be dissolved and administered in an oil-base composition or norketotifen can be dissolved in the oil phase of an oil-in-water emulsion system, which confers certain advantages to the patient, such as higher drug concentrations, improved lubrication and improved comfort to the eye.

Multiple dose or single-unit dose packages, such as for example single unit dose vials, ampoules or syringes, containing a sterile norketotifen formulation, as described herein, may be used. However, the manufacturing, handling and distribution of single-unit dose packages are expensive and the use thereof is often complicated to the patient.

Maintaining sterility in multiple-use containers is usually achieved by adding one or more preservatives to the formulations. It was an objective to develop ophthalmic formulations for patients with high IOP wherein such formulations are free from preservatives and in particular free from benzalkonium chloride (BAK), since such preservatives and in particular BAK, express target-organ toxicity, which in the case of BAK means that this particular preservative expresses toxicity that targets the trabecular mesh already within 15 minutes of exposure at concentrations of 0.0001%, which concentration is significantly lower that the concentrations that are commonly used in ophthalmic solutions.

Any toxicity targeting the trabecular mesh can decrease the filtration of aqueous humor out of the eye and increase the intraocular pressure, which is an unacceptable side effect of drugs that are used to decrease the intraocular pressure.

BAK at the extremely low concentration of 0.0001% has also been shown to stimulate macrophages, increase phagocytosis, and release cytokines and should therefore be considered as a pro-inflammatory compound, responsible for inflammation through macrophage activation. Topical application of BAK at the usual clinical concentration of 0.01% to the eye has also been found to cause corneal neurotoxicity.

In an embodiment, it has been found that ophthalmic formulations containing norketotifen are self-preserving (Example 9). The term "self-preserving" as used herein means that norketotifen and the norketotifen formulations do not support microbial growth despite the absence of any added preservative in the formulation. The term "formulations do not support microbial growth" means that the number of inoculated colonies in a formulation remain the same or decline in preservative challenge tests carried out on the formulation. A self-preserving formulation of norketotifen will not need a preservative, such as for example BAK or PHMB, to be included in the formulation.

Norketotifen ophthalmic formulations such as those shown in Table 2 are compatible with preservatives such as BAK and PHMB. Therefore, the present norketotifen formulations can be used with preservatives of various concentrations (Example 2; Table 2). It has been found that the anti-microbial effect of norketotifen is pH-dependent and formulations with acidity that is less than pH 4 may need a preservative, particularly if the concentration of norketotifen is less than about 0.02 percent. However, preservative-free ocular formulations of norketotifen are strongly preferred.

BAK (benzalkonium chloride) and other preservatives are compatible with norketotifen and there are no pharmaceutical reasons to avoid using BAK and other preservatives, such as PHMB (polyhexamethylene biguanide; polyhexanide) in ocular norketotifen formulations. However, all preferred ophthalmic formulations of norketotifen are free from preservatives and in particular free from BAK, since this common preservative excipient is known to induce various types of toxic ocular effects in concentrations as low as 0.0001% as described in the literature and in particular by the Baudouin group of independent scientists in France. Similarly, the preservative excipient PHMB, while pharmaceutically compatible with norketotifen, is expressing severe toxicity as it has been shown to affect ocular cell viability in concentrations as low as 0.0005 percent.

Micronized norketotifen can be used in intraocular compositions of norketotifen and may have particle sizes where >90 percent of the material is <10 microns. Also nanoparticles of norketotifen can be used in intraocular compositions thereof and may have particle sizes where >90 percent of the material is <1 micron. All compositions intended for use in the eye are required to be sterile. The choice of an appropriate method for manufacturing sterilization is within the scope of understanding of a person of ordinary skill in the art of manufacturing ocular dosage forms. Norketotifen compositions, which are stable at increased temperatures, can be sterilized during the manufacturing process by autoclaving. The term autoclaving relates to a standardized heating procedure characterized by heating a test composition to 120° C. to 140° C. for a period of 15 to 60 minutes, wherein the composition is aqueous. Aqueous compositions are kept in a closed vessel, which vessel is typically a plastic or glass bottle. The pressure during autoclaving is typically 1 bar to 10 bar.

It may be beneficial to adjust the compositions, shown in the examples herein in order to make the formulations autoclavable. Autoclavable ophthalmic formulations are well known and have been described for example in U.S. Pat. No. 6,776,982 that is hereby incorporated by reference. Autoclavable compositions of norketotifen are included herein.

Alternatively, intraocular norketotifen compositions can be exposed to ultraviolet rays or to irradiation, such as gamma irradiation. Formulations can also be processed aseptically, which includes filtration through sterilizing grade filters, which may have a nominal pore size of 0.22 µm and which have to be fully compatible with norketotifen and the excipients of the formulations being used.

The intra-ocular formulations containing norketotifen are intended for reduction of high IOP and in general contain norketotifen in concentrations that are significantly higher than the optimal concentrations of norketotifen that are used for the treatment of allergic conjunctivitis and xerophthalmia. For example, the present intraocular compositions for patients with high IOP, include norketotifen in concentrations of about 0.02 wt % to about 1.0 wt %, while the ophthalmic formulations of norketotifen intended for allergic conjunctivitis contain norketotifen in concentrations of 0.001 wt % to 0.3 wt % (U.S. Pat. No. 8,969,385), and ophthalmic formulations intended for xerophthalmia contain norketotifen in concentrations from 0.01 wt % to 0.5 wt % (U.S. Pat. No. 8,741,930).

Norketotifen intraocular solutions that are useful for treatment of elevated IOP and glaucoma contain about 0.02 wt % to about 1.0 wt % norketotifen, calculated as free base, as shown in Example 2. The eye-drops usually have a volume of about 50 µL.

Intraocular hydrophilic gels for treatment of elevated IOP and glaucoma contain about 0.02 wt % to about 1.0 wt % norketotifen, as shown in Example 3.

Intraocular hydrophobic ointments contain norketotifen at concentrations of about 0.02 wt % to about 1.0 wt %, as shown in Example 4.

Intraocular emulsions that are useful for treatment of high IOP contain from about 0.02 wt % to about 1.0 wt % norketotifen, shown in Example 5.

As an alternative to intraocular administration, intranasal administration is also possible to deliver norketotifen to the intraocular biophases. In one aspect, a method of treating a mammal suffering from increased intraocular pressure comprises administering an intranasal formulation comprising a therapeutically effective amount of norketotifen for the reduction of intraocular pressure to the eye of the mammal in need thereof. Norketotifen nasal solutions may contain one or more excipients as shown in Example 6 and may contain norketotifen in concentrations of about 0.02 wt % to about 1.0 wt %.

The intraocular and intranasal norketotifen compositions disclosed herein can deliver therapeutically effective concentrations of norketotifen to the tissues within the eye, which allow for once-daily intraocular administration and for repeated intraocular administrations from two to five times daily to a mammal in need thereof, while not causing ocular side effects, such as tissue toxicity, burning, redness or irritation, and while at the same time being stable upon storage.

The compositions and methods disclosed herein are intended for patients in need of medication for conditions associated with increased IOP. The terms "patient" and "mammal" refer to humans, dogs, cats and horses, for example. Preferred are human and canine patients.

Patients suffering from disorders related to high IOP include individuals being diagnosed as suffering from various types of glaucoma, such as for example open-angle glaucoma or closed-angle glaucoma, which types of glaucoma can be further subdivided into primary or secondary, as described in the reference Merck Index, 2006, which is hereby included by reference for its teaching regarding different forms of glaucoma.

As used herein, terms, such as "glaucoma", "high IOP" and "elevated IOP" refer to all forms of the diseases. As an example, some patients may have high intraocular pressure but have not developed optical nerve damage, a condition known as "ocular hypertension" that is included in the present invention. Patients with open-angle glaucoma often have no subjective symptoms, while patients with closed-angle glaucoma often have subjective symptoms, such as for example sudden eye pain, redness, nausea and/or vomiting and other symptoms resulting from acutely increased intraocular pressure.

Other known causes for elevated IOP are for example ocular infections, genetics, trauma, and side effects of certain drugs such as glucocorticosteroids. The most well-characterized disorders associated with high IOP are steroid-induced high IOP and glaucoma.

Regardless of the factors causing high IOP, this condition can lead to glaucoma and permanent loss of vision. High IOP can be treated with norketotifen regardless of the causative factors involved in the development of high IOP in humans and other mammals.

The prevalence of glaucoma in dogs varies among breeds with the highest prevalence in American Cocker Spaniel (5.4%) Chow Chow (4.7%) and Shar-Pei (4.4%) and the lowest prevalence in Cairn Terrier (1.8%) and Miniature Poodle (1.7%). Glaucoma in dogs is often treated surgically, often with laser methodology, where the laser beam selectively destroys cells that that secrete fluid into the eye. The human medications for treatment of elevated IOP are often used in canine patients. Eye drops containing norketotifen in combination with one or more of the human medications mentioned above will decrease elevated IOP in dogs. The high-IOP disease in dogs is most often called Progressive Retinal Atrophy (PRA) and is ultimately resulting in the death of the rod-cells of the retina. There are about 120 million rod-cells (responsible for vision in dim light ("night-vision"), while there are only about 6 million cone-cells (responsible for daytime vision and color-vision). Thus, PRA kills up 95 percent of the photo-cells in the canine retina.

Also included herein are methods of administering norketotifen in combination with a second drug that decreases high IOP. Some of the drugs for treatment of glaucoma decrease the production of aqueous humor in the glaucomatous eyes, while other drugs increase the outflow of aqueous humor from the eyes.

Norketotifen and the second drug can be administered separately in different formulations or can be combined in the same formulation, which may be an ocular eye-drop formulation or an intranasal formulation. Members of five classes of drugs are presently used therapeutically to decrease high ocular pressure or are under development for treatment of elevated IOP. Examples are: (1) Ophthalmic beta-adrenergic receptor antagonists, such as for example betaxolol (Beoptic® Alcon), carteolol (Teoptic® Thea Pharmaceuticals Ltd), levobunolol (Betagen® Allergan) and timolol (Timoptic® Merck & Co and generic) decrease IOP by decreasing aqueous humor production; (2) Ophthalmic alpha-adrenergic receptor agonists, such as for example epinephrine (generic), brimonidine (Alphagan-P® Allergan), dipivefrin (Propine® Allergan; AKPro® Alcorn; Pivalephrine® Santen) decrease IOP by decreasing aqueous humor production and simultaneously increasing the outflow from the eye; (3) Rho kinase (ROCK) inhibitors, such as for example ripasudil, AR-12286 and Y-39983 lower IOP by increasing the aqueous outflow; (4) Carbonic anhydrase inhibitors, such as for example acetazolamide (Azopt® Alcon and generic) are lowering IOP by decreasing the secretion of aqueous humor; and (5) Ophthalmic prostaglandin analogs, such as for example latanoprost (Xalatan® Pfizer), travoprost (Travatan® Alcon), unoprost (generic) and bimatoprost (Lumigan® Allergan) lower IOP by increasing the outflow of aqueous humor. Norketotifen can be added to the formulations of any member of the five classes mentioned above if the formulations with norketotifen has an acidity between approximately pH4.0 and approximately pH6.0.

Exemplary active agents to combine with norketotifen include as beta-adrenergic antagonists, ophthalmic alpha-adrenergic receptor agonists, Rho kinase (ROCK) inhibitors, carbonic anhydrase inhibitors and ophthalmic prostaglandin analogs. Norketotifen and the second active agent can be administered as separate ophthalmic formulations or as a combination ophthalmic or intranasal formulation.

As known by those skilled in pharmacology, the use of two compatible active ingredients, each of which are administered in a relatively low dose, may enhance the therapeutic efficacy, while the combination of two low-dose drugs may decrease the risk for side effects, when compared with the use of high doses of a single active drug.

Combination formulations containing one or more of drugs belonging to the classes listed above and one or more additional active IOP-lowering moieties are available commercially as eye-drops or can be made as eye-drops. Norketotifen can be added to formulations of drugs that are known to decrease elevated IOP or to drugs that are believed to decrease IOP if the formulations have acidity between approximately pH4.0 and approximately pH6.0.

In addition, most medications for the treatment of glaucoma are ophthalmic formulations that are administered once or several times daily. Several published studies emphasize that the medicinal compliance among glaucoma patients is poor, and one study demonstrated that 25 percent of glaucoma patients took less than 75 percent of their prescribed doses and almost 20 percent of patients took less than 50 percent of their doses, which may lead to significantly reduced efficacy of the medications and accelerated loss of vision. There are presently no approved and clinically available sustained-release drug delivery systems for glaucoma medications. However, several depot-delivery systems are under development such as Retisert® (Baush& Lomb), Ozurdex® (Allergan), Iluvien® (Alimera), ENV515 (Envisia Therapeutics), Helios® (ForSight Vision), TODDD® (Vista Scientific). It is expected that one or more of the new depot delivery systems for ocular medications will be compatible with norketotifen or a salt of norketotifen.

The invention is further illustrated by the following non-limiting examples.

EXAMPLES

Example 1: Aqueous Solubility of Norketotifen

Norketotifen HF was weighed in excess, added to 5 mL of water, adjusted to predetermined acidity and stirred at room temperature overnight. The concentrations of norketotifen in the supernatants were determined by HPLC using a Waters Symmetry® C18 column, 3.9×150 mm.

TABLE 1

Solubility of norketotifen in water as a function of acidity

| pH | Norketotifen solubility (%) |
|---|---|
| 3.7 | 0.22 |
| 3.7-8.5 | 0.22 |
| 8.6 | 0.21 |
| 8.75 | 0.14 |
| 10.0 | 0.04 |

The solubility of norketotifen was enhanced by the addition of excipients, such as for example, polysorbate 80 or Pluronic P-123. In a separate study, the water solubility of norketotifen was significantly increased by addition of 5 percent of Pluronic P-123 or 5% of polysorbate 80, and by combinations of these solubilizers.

Pluronic P-123 is a tri-block copolymer with the formula

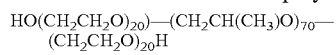

It was concluded that the aqueous solubility of norketotifen was about 0.22% in the acidity range that is used for ocular solutions and the solubility was improved by various solubilizing excipients, such as for example EDTA, polysorbates and Pluronic-123.

Example 2. Aqueous Solutions of Norketotifen for Intraocular Indications

In specific embodiments, intraocular formulations containing norketotifen and intended for intraocular use are free from preservatives such as the preservative-free NOBAK/G formulations in Table 2.

The solution formulations were prepared by adding the excipients one at a time to an appropriate amount of water, followed by mixing until dissolved. Once all excipients had been added and dissolved, norketotifen was added to the solution of excipients and mixed continuously until dissolved.

Intraocular solutions may be designed for once-daily ocular administration or for repeated ocular administrations from two to five times daily. Aqueous intraocular solutions generally include about 0.02 wt % to about LO wt % of norketotifen free base equivalent.

An eyedropper device is usually used for the administration of ophthalmic solutions to the eye. The device is usually a glass bottle with a separate eyedropper or a squeezable plastic dropper. The volume of each drop depends on the construction of the device, the technique used to produce the drop and the viscosity of the solution being administered. Eyedroppers usually deliver drops with a volume of about 50 µL. The total dose of norketotifen delivered to the eye depends on the volume of the eye drops (usually 50 µL) and the concentration of norketotifen in the formulation (see Table 2).

Example 3: Hydrophilic Gels/Ointments of Norketotifen for Intraocular Indications As used herein, the terms "gel" and "ointment" are synonyms.

Intraocular gel compositions containing norketotifen are intended to keep the drug in the eye for an extended period

TABLE 2

Examples of norketotifen HF and norketotifen FB solution formulations for intraocular administration. All concentrations and all pH-values are approximate.

| Component | NOBAK/G, (wt %) | LOBAK/G, (wt %) | MIDBAK/G, (wt %) | HIBAK/G, (wt %) | PHMB/G, (wt %) |
|---|---|---|---|---|---|
| Norketotifen HF or | 0.414 (*) | 0.414 (*) | 0.414 (*) | 0.414 (*) | 0.414 (*) |
| Norketotifen FB (1) | 0.300 | 0.300 | 0.300 | 0.300 | 0.300 |
| EDTA or | 0.05-0.4 | 0.05-0.4 | 0.05-0.4 | 0.05-0.4 | 0.05-0.4 |
| Polysorbate 80 or | 0.5-5.0 | 0.5-5.0 | 0.5-5.0 | 0.5-5.0 | 0.5-5.0 |
| Poloxamer (PX) | 0.1-1.0 | 0.1-1.0 | 0.1-1.0 | 0.1-1.0 | 0.1-1.0 |
| Boric Acid | 0.095 | 0.095 | 0.095 | 0.095 | 0.095 |
| BAK | — | 0.001 | 0.005 | 0.010 | — |
| PHMB | — | — | — | — | 0.0001 |
| Sorbitol | 4.600 | 4.600 | 4.600 | 4.600 | 4.600 |
| Aq. Dest. | q.s. | q.s. | q.s. | q.s. | q.s. |
| pH | 4.0-6.0 | 4.0-6.0 | 4.0-6.0 | 4.0-6.0 | 4.0-6.0 |

(1) Norketotifen hydrogen fumarate (HF) 0.414 % is equivalent to norketotifen free base (FB) 0.300 %.
(*) Useful concentrations of norketotifen in solutions are from about 0.01 wt% to about 1.0 wt% (calculated as FB); specific concentrations of norketotifen are about 0.02 wt% to 0.9 wt% (calculated as FB).
BAK = benzalkonium chloride.
PHMB = polyhexamethylene biguanide.

The final viscosity was adjusted by the addition of a thickening agent, such as for example one or more polyethylene glycols (PEG), a polysorbate or a pluronic to obtain the preferred viscosity. The final acidity can be adjusted by the addition of for example 1-N sodium hydroxide (NaOH) or 1-N hydrochloric acid (HCl).

Intraocular solutions may contain norketotifen and excipients at concentrations that are different from those shown in Table 2. Intraocular solutions may contain excipients that are different from those shown in Table 2.

of time and the prolonged exposure will enhance drug delivery. Intraocular gels can be hydrophilic or hydrophobic.

An example of an exemplary composition for a hydrophilic intraocular gel containing norketotifen hydrogen fumarate (HF) is shown in Table 3.

Intraocular hydrophilic gels may contain norketotifen and excipients at concentrations that are different from those shown in Table 3. Intraocular hydrophilic ointments or gels containing norketotifen may contain excipients that are different from those shown in Table 3.

Intraocular hydrophilic gels for use in patients suffering from increased intraocular pressure may contain norketotifen at concentrations between about 0.02 wt % and 1.0 wt %. The gel formulations have a viscosity of 5,000 to 500,000 cP, specifically 20,000 to 200,000 cP. Examples of thickeners/gelling/agents are polyethylene glycol 300, polyethylene glycol 3350, polyethylene sorbate (polysorbate), chitosan and edetate (EDTA). A compatible surfactant, such as for example poloxamer 407 can also be added, for example in a concentration less than 25 percent, more preferred in a concentration less than 20 percent by weight. It was also found that the gels could contain additional excipients, such as humectants such as for example sorbitol, viscosity modifying agents such as for example methyl cellulose, tonicity modifying agents such as for example NaCl and/or propylene glycol, chelating agents such as for example polysaccharides, buffers such as for example phosphate buffers, surfactants such as for example glyceryl stearate, mucoadhesives such as for example polyisobutylcyanoacrylate (PIBCA) and/or antioxidants such as for example butylated hydroxyanisole (BHA) or butylated hydroxytoluene (BHT).

Intraocular hydrophilic gels were designed for once-daily ocular administration or for repeated administrations from two to five times daily.

The selected hydrophilic gel in Table 3 is thick but miscible with water. Compositions like those shown in Table 3 can hold the drug product in the eye of the patient for an extended time, which will enhance the intra-ocular drug delivery to the biophase(s).

TABLE 3

An example of a topical hydrophilic intraocular gel containing norketotifen.

| Component | Batch O/G1009, wt% |
|---|---|
| Norketotifen HF (%) or | 0.552 |
| norketotifen FB (%) | 0.400 |
| PEG 300 (%) if norketotifen HF is used or | 69.448 |
| PEG 300 (%) if norketotifen FB is used | 69.600 |
| PEG 3350 (%) | 30.000 |

HF = hydrogen fumarate (salt).
FB = free base

Batch O/G1009 used a mixture of the polyethylene glycols PEG 300 and PEG 3350 as solvent for norketotifen.

The composition of Table 3 was prepared by adding the two polyethylene glycols to a suitable container and heating to 60-65° C. This heating step melts the high molecular weight polyethyleneglycols. Next, norketotifen was added and the composition was mixed until the active ingredient was dissolved. Finally, the composition was cooled with mixing to allow the ointment/gel to thicken. The viscosity was 30,000 cP or greater. The pH range for these compositions was not measured since the formulations were non-aqueous. If needed, the tonicity can be adjusted by adding a tonicity-adjusting agent to obtain the desired tonicity. If wanted, a preservative can be added, however, no preservative will be needed when the concentration of norketotifen is equal or higher than about 0.02% and the acidity is equal to or higher than about pH 4.0 when diluted by about 1 to 3 parts by 10 in water and measured using a standardized pH electrode.

The concentration of norketotifen can be from about 0.02 wt % to about 1.0 wt % if dissolved in excipients, such as for example PEG 300, PEG 3350 or a mixture of polyethylene glycols.

A squeezable tube with a small tip is usually used for the administration of gels or ointments to the eye. The amount administered depends on the technique used and the design of the tube. The amount of the gel or ointment dosed is usually at about 20 mg to about 50 mg for each application.

Example 4: Hydrophobic Gels/Ointments of Norketotifen for Intraocular Indications An example of hydrophobic intraocular ointments containing norketotifen hydrogen fumarate (HF) is shown in Table 4.

Hydrophobic intraocular ointments may contain norketotifen and excipients at concentrations that are different from those shown in Table 4. Hydrophobic intraocular ointments containing norketotifen may contain excipients that are different from those shown in Table 4.

The tested hydrophobic ointments were not miscible with water. These compositions can hold the drug product in the eye of the patient for an extended time, which will enhance the delivery of norketotifen to the intra-ocular biophase(s).

Intraocular hydrophobic ointments may contain norketotifen at concentrations of about 0.02 wt % to about 1.0 wt %. The intraocular hydrophobic ointments have a viscosity of about 1,000 to about 500,000 cP, specifically about 20,000 to about 200,000 cP. Ophthalmic hydrophobic ointments have tonicity of about 150 and about 450 mOsm, specifically about 230 and about 330 mOsm. The intraocular hydrophobic ointments can also contain other excipients, such as humectants, viscosity modifying agents, tonicity agents, chelating agents, buffers, surfactants, mucoadhesives, antioxidants and preservatives. The intraocular hydrophobic ointments and gels were designed for once-daily ocular administration or for repeated ocular administrations from two to five times daily to a mammal in need thereof

TABLE 4

An example of a hydrophobic ointment containing norketotifen HF.

| Component | Batch 1012/G, wt% |
|---|---|
| Norketotifen HF (%) | 0.552 (1) |
| Propylene glycol (%) | 2.500 |
| Glyceryl stearate (%) | 0.500 |
| Cetyl alcohol (%) | 0.500 |
| White petrolatum | q.s. |

Norketotifen HF (hydrogen fumarate) 0.552% is equivalent to norketotifen FB (free base) 0.400%.

Batch 1012/G contained propylene glycol as a solvent for norketotifen, glyceryl stearate and cetyl alcohol as surfactants and white petrolatum as base.

The hydrophobic ointment was prepared by dissolving norketotifen in propylene glycol. Next, glyceryl stearate, cetyl alcohol, and white petrolatum were added to a suitable container and heated to 65-70° C. This heating step melts the surfactants and the petrolatum. Next, the norketotifen solution was slowly added and the composition mixed until the solvent was dispersed. Finally, the composition was cooled with mixing to allow the ointment to thicken.

If desired, acidity can be adjusted by adding an acid or a base to obtain the preferred acidity. If desired, tonicity can be adjusted by adding a tonicity-adjusting agent to obtain the preferred tonicity. If desired, viscosity can be adjusted by a viscosity-modifying agent to obtain the preferred viscosity. If desired, a preservative can be added, however, no preservative is needed when the concentration of norketotifen is equal or higher than about 0.02%.

Example 5. Emulsions of Norketotifen for Intraocular Indications

An example of an intraocular emulsion containing norketotifen hydrogen fumarate (HF) is shown in Table 5. Batches E1115/G did not contain preservatives since norketotifen is potently self-preserving. Intraocular norketotifen emulsions may contain norketotifen excipients that are different from those shown in Table 5. Intraocular emulsions may contain norketotifen and excipients at concentrations that are different from those shown in Table 5.

Useful intraocular emulsions contained norketotifen at concentrations of about 0.02 wt % to about 1.0 wt %. The intraocular emulsions had a viscosity of about 1.0 to about 300,000 cP, specifically about 2.0 to about 90,000 cP, most specifically about 2.5 to about 75,000 cP. The intraocular emulsions had osmolality of about 150 to about 450 mOsm, specifically about 230 to about 330 mOsm. The intraocular emulsions had pH of about 4 to about 6.5, specifically of about pH 5.0 to about pH 6.0. The intraocular emulsions may also contain excipients, such as humectants, viscosity modifying agents, tonicity agents, chelating agents, buffers, muco-adhesives, surfactants and antioxidants. If wanted, a preservative can be added, however, no preservative will be needed when the concentration of norketotifen is greater than or equal to about 0.02 wt % and the pH is about pH 4.0 to about pH 6.0.

TABLE 5

Example of an ophthalmic norketotifen emulsion for intraocular indications

| Norketotifen and excipients in per cent | E1115/G |
|---|---|
| Norketotifen HF or | 0.552 |
| Norketotifen FB | 0.400 |
| Sodium phosphate dibasic | 0.160 |
| Propylene glycol | 1.850 |
| Castor oil | 1.250 |
| Polyoxyl 35 castor oil | 1.000 |
| Methylcellulose | |
| 1.0 N HCl or | q.s. to target pH |
| 1.0 N NaOH | |
| Water | q.s. |
| pH | 5.5 |

Norketotifen HF (hydrogen fumarate) 0.552% is equivalent to norketotifen FB (free base) 0.400%;
q.s. = quantum sufficit (as needed).

Batch E1115/G contained a phosphate buffer, and propylene glycol as a solvent/moisturizer/tonicity modifier. This batch also contained castor oil and polyoxyl castor oil as surfactants. Several batches were made and the acidity was adjusted over a wide range. It was determined that emulsions can be used at pH of about 4.0 to about 6.5; the preferred range was about pH 5.0 to about pH 6.0.

The selected emulsions in Table 5 were prepared by adding propylene glycol, castor oil, ethoxylated castor oil, and water to a suitable container. The contents of the container were sonicated with a ½" ultrasonic probe for 20 minutes. The resulting emulsion droplets were mostly less than 0.5 microns. The emulsion was filtered through a 0.22-micron cellulose acetate filter. After filtration, norketotifen and buffer were added.

If needed, the tonicity can be adjusted by adding a tonicity-adjusting agent to obtain the preferred tonicity. The viscosity of norketotifen emulsions can be adjusted by the addition of one or more compatible viscosity-modifying agents as needed to obtain the preferred viscosity.

Intraocular emulsions may contain norketotifen and excipients at concentrations that are different from those shown in Table 5. Intraocular emulsions containing norketotifen may contain excipients that are different from those shown in Table 5.

Example 6: Intranasal Administration of Norketotifen for Intraocular Indications Administration of an intranasal formulation of norketotifen onto the highly vascularized 150 cm$^2$ epithelial surface of the human nasal cavity results in rapid systemic absorption and rapid transport of drugs to intraocular tissues. While topical application to the intraocular tissues is delayed by penetration barriers, norketotifen is rapidly transported to the eye by the blood after intranasal administration. Intranasal administration can be used to avoid ocular irritation in sensitive individuals. Intranasal administration can be achieved by use of drops of a solution of norketotifen or by use of a nasal spray applicator. This type of nasal applicator usually delivers about 0.05 mL to about 0.5 mL of a solution formulation in each metered spray. Useful intranasal solutions may contain from about 0.022 wt % to about 1.0 wt % of norketotifen, expressed as the free base, but administered either as the free base or as a salt, such as a hydrogen fumarate salt. An exemplary formulation is an intranasal solution containing 0.4 wt % to 1.0 wt % of norketotifen that is administered in about 0.1 mL of a nasal solution. In addition to norketotifen, the intranasal formulation may contain disodium phosphate (as a buffer), polysorbate 80 (improving the solubility of norketotifen), EDTA (gelling agent), NaCl (for adjustment of tonicity), and water. The acidity of nasal formulations of norketotifen may be about pH 4.0 to about pH 6.0. Self-preserving norketotifen formulations can be used without an added preservative. Intranasal solutions may be designed for once-daily nasal administration or for repeated nasal administrations from two to five times daily.

Example 7: Ocular Irritation/Toxicity Study of Norketotifen

Fifty-two rabbits (26F+26M) were assigned to four groups and were administered repeated daily doses of norketotifen HF solutions by the ocular route, 0.00, 0.0345, 0.0690 and 0.138 wt % for 6 weeks. Two recovery weeks (without dosing of norketotifen) were added to the six weeks of norketotifen 0.138% dosing. In addition to regular toxicology parameters, ophthalmic parameters and ocular irritation scores were assessed. Blood samples were collected at predetermined time intervals. Plasma sample were analyzed using a validated LCMS-MS method. Plasma pharmacokinetics was calculated.

The study results demonstrated that there were no test article-related adverse events by norketotifen during this study, and the No-Observable-Adverse-Effect-Level (NOAEL) for this study was 0.138% of norketotifen HF (the highest concentration tested).

Example 8: Effects of Norketotifen on Intra-Ocular Pressure (IOP)

In the previously described Ocular Irritation/Toxicity Study (Example 7), intraocular pressure was measured in the eyes of one group of rabbits (3M+3F), before, during and after repeated daily ocular treatment with norketotifen eye-drops. Surprisingly—and as shown in Table 6—there was a highly significant decrease in IOP when the animals were treated with norketotifen eye-drops. The group tested for effects on IOP consisted of 12 eyes and the dose administered was 0.14 wt % and norketotifen was administered daily for 6 weeks, followed by a two-week recovery period without norketotifen administration. Day 42 was the last day of the treatment period and Day 56 was the last day of the recovery period.

TABLE 6

Effects of norketotifen HF on TOP in 6 rabbits

|  | Day 1 (pretest) | Day 42 (treatment) | Day 56 (recovery) |
|---|---|---|---|
| IOP (mm Hg; ± SD) | 20.4 ± 2.9 | 16.5 ± 1.7 | 20.5 ± 1.6 |
| Student's t-test | Day 1 vs. Day 42 P = 0.0005 | — | Day 42 vs. Day 56 P < 0.0001 |

The mechanism for the IOP-lowering effect of norketotifen is unknown. Studies in rabbits have demonstrated IOP-lowering effects of drugs, such as for example the adrenergic beta-blocker timolol that is known to decrease the intra-ocular secretion of aqueous humor and by drugs that are known to improve the drainage of the aqueous humor, such as for example the prostaglandin analog latanoprost.

Example 9: Antimicrobial Effectiveness Testing

Ophthalmic products in multi-dose containers must be adequately preserved to prevent contamination during repeated use. The most commonly used preservative, benzalkonium chloride (BAK) has known and much feared side effects on the eye as described the Baudouin group in France.

METHOD: The standardized Preservative Challenge Test (U.S. Pharmacopeia 51 Antimicrobial Effectiveness Testing) have been used for tests of self-preservation by norketotifen in concentrations to be used for patients suffering from allergic conjunctivitis and xerophthalmia. USP (51) is a standard test used to determine the antimicrobial effectiveness of test articles and ophthalmic formulations. The present tests were using 150 ml of each formulation and covered the mandatory five organisms: *Escherichia coli* (fermentative G−), *Pseudomonas aeruginosa* (non-fermentative G−), *Staphylococcus aureus* (G+), *Aspergillus brasiliensis* (mold), and *Candida albicans* (yeast). The number of inoculated cells was $0.5 \times 10^5$ per mL and the incubation temperature was 25° C. for all inoculations. Plating for measuring of recoveries were performed weekly over 4 weeks. The norketotifen formulations were defined as being self-preserving only if the numbers of cell colonies remained constant (fungi) and were declining (bacteria) according to the strictly standardized USP 51 protocol. Tests were performed at pH 4.0, pH 4.5, pH 5.0 and pH 6.0 and the test articles were dissolved in BSA/water (BSA=bovine serum albumin) containing at least 0.01 percent norketotifen (calculated as free base). All solutions used in the antimicrobial studies were devoid of added preservatives.

USP Criteria for Tested Microorganisms (Category 1)

Bacteria: Not less than a 3.0 logarithmic reduction from the initial count to the count at 14 days, and no increase from the counts at 14 days to the counts at 28 days.

Yeast and Molds (Fungi): No increase from the initial calculated count at 14 or 28 days.

RESULTS: Recent studies using concentrations intended for the elevated IOP indication demonstrated improved self-preservation by norketotifen. When tested at therapeutic concentrations, norketotifen was found to be self-preserving at all levels of acidity tested (pH 4.0 to pH 6.0). Thus, the numbers of colonies of all five microorganisms declined or stayed the same during the course of the 4-week tests of norketotifen in formulations with pH 4.0 to pH 6.0.

TABLE 7

Results from preservation challenge tests of formulations containing low therapeutic concentrations of RS-norketotifen

| FORMULATION | pH 4.0 | pH 4.5 | pH 5.0 | pH 6.0 |
|---|---|---|---|---|
| NORKETOTIFEN; NOBAK or BSA/water | ***** | ***** | ***** | ***** |

***** indicates that for all five microorganisms the numbers of colonies declined or remained constant according to <USP 51>. All norketotifen formulations passed the tests.

TABLE 8

Results from preservation challenge tests of formulations containing therapeutic concentrations of RS-norketotifen hydrogen fumarate and RS-ketotifen (in saline formulations; pH adjusted to 5.0).

| TA; pH | Contact Time | Data Description | E. coli | P. aerugin | S. aureus | A. brasil | C. albic |
|---|---|---|---|---|---|---|---|
| NORK pH 5.0 | Day 0 | CFU/ml | 8.5E+05 | 4.7E+05 | 2.5E+05 | 7.0E+05 | 6.0E+05 |
|  | Day 14 | CFU/ml | <5.0+00 | <5.0+00 | <5.0+00 | 5.75E+02 | <5.0+00 |
|  |  | Log Reduc | >5.23 | >4.79 | >4.70 | 3.09 | >5.08 |
|  | Day 28 | CFU/ml | <5.0+00 | <5.0+00 | <5.0+00 | 3.10E+02 | <5.0+00 |
|  |  | Log Reduc | >5.23 | >4.97 | >4.70 | 3.35 | >5.08 |
| KETO pH 5.0 | Day 0 | CFU/ml | 1.5E+06 | 3.1E+05 | 2.0E+06 | 3.6E+05 | 7.9E+05 |
|  | Day 14 | CFU/ml | 2.5E+04 | 1.5E+4 | 3.3E+06 | 4.8E+05 | 3.0E+03 |
|  |  | Log Reduc | 1.78 | 1.31 | None | None | 1.1E+03 |
|  | Day 28 | CFU/ml | 2.6E+06 | 2.3E+05 | 3.6E+06 | 2.0E+05 | 1.1E+03 |
|  |  | Log Reduc | None | 0.13 | None | 0.25 | 0.25 |

NORK = RS-norketotifen hydrogen fumarate.
KETO = RS-ketotifen hydrogen fumarate.
CFU = Colony-Forming-Units;
*E. coli* = *Escherichia coli*;
*P. aerugin* = *Pseudomonas aeruginosa*;
*S. aureus* = *Staphylococcus aureus*;
*A. brasil* = *Aspergillus brasiliensis*;
*C. albic* = *Candida albicans*

CONCLUSION

The ocular formulation of norketotifen at concentrations that are useful for decreasing IOP was self-preserving and can therefore be used without preservatives. The ocular formulation of ketotifen did not pass the test criteria for any of the micro-organisms and did therefore not pass the self-preservation test and can therefore not be used without preservatives.

The terms "about" and "approximately" and "approximate" in the context of concentrations means±10%. Thus, approximately 2.0 mg/ml means 2.0±0.2 mg/ml and about 3.0 percent means 3.0±0.3 percent.

The terms "about" and "approximately" and "approximate" in the context of acidity means±0.1 pH unit. Thus, "approximately pH 6.0" means from pH 5.9 to pH 6.1.

The term "biophase" means "site of action".

The terms "composition" and "formulation" are used as synonyms herein.

Ophthalmic formulations that are designed to deliver norketotifen to the intraocular biophases are herein referred to as "intraocular formulations".

If not stated to the contrary, all percent concentrations in this document refer to percentage by weight (w/w or wt %).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treating a mammal in need of a reduction in intraocular pressure, comprising
    administering an intraocular formulation comprising a therapeutically effective amount of norketotifen for the reduction of intraocular pressure to the eye of the mammal in need thereof, wherein the intraocular formulation comprises about 0.02 wt % to about 1.0 wt % norketotifen or a salt or an isomer thereof, wherein the amount of norketotifen is calculated as the norketotifen free base,
    wherein the intraocular formulation is free from any added preservative, wherein the intraocular formulation is self-preserving,
    wherein the mammal has glaucoma with high intraocular pressure.

2. The method of claim 1, wherein the ophthalmic formulation is in the form of an aqueous solution having a pH of about pH 4 to about pH 6, a hydrophilic gel, a hydrophobic ointment, or an emulsion.

3. The method of claim 1, wherein the ophthalmic formulation comprises one or more of a chelating agent, a stabilizing agent, a buffering agent, a tonicity adjusting agent, a solubilizing agent, a viscosity-adjusting agent, a humectant, an-antioxidant, a gelling agent, an in situ gelling agent, a lubricant, a mucoadhesive agent, a surfactant, or a combination thereof.

4. The method of claim 1, further comprising administering an ophthalmic adrenergic beta-adrenergic receptor antagonist, wherein the norketotifen and the adrenergic beta-adrenergic receptor antagonist are administered in the same formulation or in different formulations.

5. The method of claim 1, further comprising administering an ophthalmic adrenergic alpha-adrenergic receptor agonist, wherein the norketotifen and the adrenergic alpha-adrenergic receptor agonist are administered in the same formulation or in different formulations.

6. The method of claim 1, further comprising administering an ophthalmic Rho-kinase (ROCK) inhibitor, wherein the norketotifen and the ROCK inhibitor are administered in the same formulation or in different formulations.

7. The method of claim 1, further comprising administering an ophthalmic carbonic anhydrase inhibitor, wherein the norketotifen and the carbonic anhydrase inhibitor are administered in the same formulation or in different formulations.

8. The method of claim 1, further comprising administering an ophthalmic prostaglandin analog, wherein the norketotifen and the prostaglandin analog are administered in the same formulation or in different formulations.

9. The method of claim 1, wherein the mammal is a human patient.

10. The method of claim 1, wherein the mammal is a canine patient.

11. A method of treating a human in need of a reduction in intraocular pressure, comprising
    administering an intranasal formulation comprising a therapeutically effective amount of norketotifen for the reduction of intraocular pressure to the eye of the human in need thereof, wherein the intranasal formulation comprises about 0.02 wt % to about 1.0 wt % norketotifen, a salt or isomer thereof, wherein the amount of norketotifen is calculated as the norketotifen free base,
    wherein the human has glaucoma with high intraocular pressure.

12. The method of claim 11, wherein the intranasal formulation is free from added preservative, wherein the intranasal formulation is self-preserving.

13. The method of claim 11, wherein the mammal is a human patient.

* * * * *